United States Patent [19]

Takagawa et al.

[11] Patent Number: 5,068,480
[45] Date of Patent: Nov. 26, 1991

[54] PROCESS FOR PRODUCING 2,6-DIMETHYLNAPHTHALENE

[75] Inventors: Makoto Takagawa; Ken Yamagishi; Jyun Yoshihara; Kenji Inamasa; Kumiko Watabe, all of Niigata, Japan

[73] Assignee: Mitsubishi Gas Chemical Company, Inc., Tokyo, Japan

[21] Appl. No.: 621,260

[22] Filed: Dec. 3, 1990

[30] Foreign Application Priority Data

Dec. 2, 1989 [JP] Japan .................................. 1-310571
Feb. 27, 1990 [JP] Japan .................................. 2-46857

[51] Int. Cl.$^5$ .................................................. C07C 5/00
[52] U.S. Cl. .................................... 585/411; 585/407; 585/320; 502/60
[58] Field of Search ............... 585/411, 407, 417, 320; 502/60

[56] References Cited

U.S. PATENT DOCUMENTS 3,931,348 6/1976 Taniguchi et al. .................. 585/411

FOREIGN PATENT DOCUMENTS 0362507 4/1990 European Pat. Off. .

Primary Examiner—Asok Pal
Assistant Examiner—P. N. Achutamurthy
Attorney, Agent, or Firm—Wenderoth, Lind & Ponack

[57] ABSTRACT

A process for producing 2,6-dimethylnaphthalene, which comprises subjecting 2-methyl-1-(p-tolyl)-butene, 2-methyl-1-(p-tolyl)-butane or a mixture of these to cyclization and dehydrogenation in the presence of a catalyst comprising lead oxide and/or indium oxide and aluminum oxide.

9 Claims, No Drawings

PROCESS FOR PRODUCING 2,6-DIMETHYLNAPHTHALENE

FIELD OF THE INVENTION

This invention relates to a catalyst for producing 2,6-dimethylnaphthalene useful as a starting material for 2,6-naphthalenedicarboxylic acid.

2,6-Naphthalenedicarboxylic acid has an industrially important use as a starting material for a high-performance polyester used for the production of polyethylene naphthalate fibers, films, etc., which have excellent tensile strength and heat resistance.

DESCRIPTION OF PRIOR ARTS 2,6-Dimethylnaphthalene is used as a starting material for 2,6-naphthalenedicarboxylic acid, and required to be producible in a large amount and at a low cost. And, since 2,6-naphthalenedicarboxylic acid as a starting material for a high-performance polyester is required to be highly pure isomerically, 2,6-dimethylnaphthalene as a starting material therefor is also required to be highly pure isomerically. That is, since dimethylnaphthalene has nine isomers of 1,2-, 1,3-, 1,4-, 1,5-, 1,6-, 1,7-, 1,8-, 2,3- and 2,7-forms in addition to the 2,6-form, it is necessary to produce a 2,6-dimethylnaphthalene in a large amount and at a low cost, which production is substantially free from formation of such isomers other than 2,6-dimethylnaphthalene.

2,6-Dimethylnaphthalene has been heretofore produced by isolating it from a tar fraction. However, the amount of 2,6-dimethylnaphthalene that can be produced from a tar fraction is small, and due to a large content of an isomer mixture, its separation or purification is difficult. It is therefore difficult to industrially provide 2,6-dimethylnaphthalene in a large amount and at a low cost by separating it from a tar fraction.

In recent years, various processes for synthesizing 2,6-dimethylnaphthalene from a variety of materials have been proposed. However, no industrial process which permits effective and selective synthesis of 2,6-dimethylnaphthalene from an inexpensive material available in a large amount has been developed.

For example, Japanese Laid-Open Patent Publication No. 18856/1974 discloses a process for the production of 2,6-dimethylnaphthalene, in which dimethyltetralin is dehydrogenated and then isomerized. This process, however, involves a problem in that dimethyltetralin as a starting material cannot be obtained easily. Namely, the amount of dimethyltetralin that can be produced from a tar fraction is small, the yield of dimethyltetralin by a method of cyclization of alkyl or alkenyl benzenes is low, and due to formation of isomers other than 2,6-dimethylnaphthalene, isomerization and isolation from an isomer mixture are required to obtain the intended 2,6-dimethylnaphthalene.

Japanese Laid-Open Patent Publication No. 112527/1988 discloses a production process in which naphthalene or methylnaphthalene is methylated. Even in this process, it is difficult to selectively obtain 2,6-dimethylnaphthalene, and an isomerization reaction and separation from an isomer mixture are required. Further, naphthalene and methylnaphthalene are all limited in availability and hence expensive as an industrial material.

Japanese Patent Publications Nos. 17983/1975, 17984/1975 and 17985/1975 disclose a process for the production of 2,6-dimethylnaphthalene, in which 5-(o-tolyl)pentene-2 as a starting material is dehydrogenated and cyclized. This 5-(o-tolyl)pentene-2 is generally synthesized from o-xylene and 1,3-butadiene. However, when the synthesis of 5-(o-tolyl)pentene-2 is carried out by side-chain alkylation, the synthesis itself is not easy. That is, according to Example in Japanese Patent Publication No 17985/1975, dehydrogenation and cyclization of 5-(o-tolyl)pentene-2 involve formation of dimethylnaphthalene having 1,5- and 1,6-forms to a great extent in addition to 2,6-dimethylnaphthalene. It is therefore required to isomerize dimethylnaphthalene having 1,5- and 1,6-forms and isolate and purify an isomer mixture in order to obtain 2,6-dimethylnaphthalene.

As a process for the production of 2,6-dimethylnaphthalene by cyclization and dehydrogenation of 2-methyl-1-(p-tolyl)-butene, U.S. Pat. No. 3,931,348 discloses a process which is carried out in the presence of a catalyst comprising rhenium oxide, alkali metal oxide or alkaline earth metal oxide and alumina, and another process which is carried out in the presence of a chromia.alumina-based catalyst containing alkali metal oxide. However, even if any one of these catalysts is used, the yield of 2,6-dimethylnaphthalene is low, and the isomeric purity of the formed 2,6-dimethylnaphthalene is not satisfactory.

In the above conventional processes, it is difficult to produce isomerically pure 2,6-dimethylnaphthalene suitable for the production of 2,6-naphthalenedicarboxylic acid at a low cost and in a large amount.

As a process which can replace the above conventional processes, a process for producing 2,6-dimethylnaphthalene through p-tolyl-sec-butyl ketone from such generally used materials as toluene, butene and carbon monoxide, as starting materials was found, and applied for a patent (EP 0.362,507).

That is, in the above process, 2,6-dimethylnaphthalene is produced by synthesizing p-tolyl-sec-butyl ketone from toluene, butene and carbon monoxide, hydrogenating the carbonyl group of the p-tolyl-sec-butyl ketone to form the corresponding alcohol, dehydrating the alcohol to prepare 2-methyl-1-(p-tolyl)butene, and cyclizing and dehydrogenating the 2-methyl-1-(p-tolyl)-butene.

The above process comprises four steps of acylation, hydrogenation, dehydration, and a combination of cyclization and dehydrogenation. Each of the acylation, hydrogenation and dehydration steps proceeds at high yields with high selectivity, and 2-methyl-1-(p-tolyl)butene can be therefore obtained at high yields. However, the last, cyclization and dehydrogenation step using a chromia.alumina-based catalyst containing alkali metal oxide cannot be said to be satisfactory in view of the yield of 2,6-dimethylnaphthalene, and it has been therefore desired to improve this last step.

SUMMARY OF THE INVENTION

It is an object of this invention to provide a process for producing 2,6-dimethylnaphthalene from such generally used materials as toluene, butene and carbon monoxide, as starting materials nearly free from formation of isomers other than 2,6-dimethylnaphthalene and at high yields.

It is another object of this invention to provide a process for producing 2,6-dimethylnaphthalene through p-tolyl-sec-butyl ketone nearly free from formation of isomers other than 2,6-dimethylnaphthalene and at high yields.

It is further another object of this invention to provide a process for producing 2,6-dimethylnaphthalene from 2-methyl-1-(p-tolyl)-butene, 2-methyl-1-(p-tolyl)-butane or a mixture of these with an isomerically high purity and at high yields.

It is yet another object of this invention to provide a process for producing 2,6-dimethylnaphthalene nearly free from formation of isomers other than 2,6-dimethylnaphthalene at a low cost and with ease.

Further, it is another object of this invention to provide a process for producing 2,6-dimethylnaphthalene, which permits cyclization and dehydrogenation reactions in the presence of water.

According to this invention, there is provided a process for producing 2,6-dimethylnaphthalene, which comprises subjecting 2-methyl-1-(p-tolyl)-butene, 2-methyl-1-(p-tolyl)-butane or a mixture of these to cyclization and dehydrogenation in the presence of a catalyst comprising lead oxide and/or indium oxide and aluminum oxide.

DETAILED DESCRIPTION OF THE INVENTION

The present inventors have made a diligent study to produce 2,6-dimethylnaphthalene having an isomerically high purity from 2-methyl-1-(p-tolyl)-butene, etc., at high yields, and found that 2,6-dimethylnaphthalene having an isomerically high purity can be produced at high yields in the presence of a catalyst comprising, as basic components, indium oxide and aluminum oxide and/or lead oxide, and aluminum oxide. Thus, this invention has been arrived at on the basis of the above finding.

This invention relates to a process for producing 2,6-dimethylnaphthalene by subjecting 2-methyl-1-(p-tolyl)-butene, 2-methyl-1-(p-tolyl)-butane or a mixture of these to cyclization and dehydrogenation in the presence of (a) a catalyst comprising lead oxide and/or indium oxide and aluminum oxide, (b) a catalyst comprising lead oxide and/or indium oxide, aluminum oxide and oxide of at least one member selected from the group consisting of alkali metals and alkaline earth metals, (c) a catalyst comprising lead oxide and/or indium oxide, aluminum oxide and oxide of at least one member selected from the group consisting of iron, tin, antimony, chromium, zinc, vanadium, nickel and cobalt, or (d) a catalyst comprising lead oxide and/or indium oxide, aluminum oxide, oxide of at least one member selected from the group consisting of iron, tin, antimony, chromium, zinc, vanadium, nickel and cobalt and oxide of at least one member selected from the group consisting of alkali metals and alkaline earth metals.

It has been found that the use of a mixed catalyst of lead oxide and/or indium oxide and aluminum oxide greatly improves the formation of 2,6-dimethylnaphthalene in the cyclization and dehydrogenation of 2-methyl-1-(p-tolyl)-butene, etc., and nearly completely inhibits the formation of dimethylnaphthalenes other than 2,6-dimethylnaphthalene under a cyclization and dehydrogenation condition, whereby this invention has been completed.

That is, in the case of using aluminum oxide alone as a catalyst, part of 2-methyl-1-(p-tolyl)-butene is converted to dimethylnaphthalene by cyclization and dehydrogenation, but undergoes isomerization extraordinarily, and unintended reactions such as polymerization and decomposition overwhelmingly take place. When lead oxide and/or indium oxide are used alone as a catalyst, the cyclization and dehydrogenation of 2-methyl-1-(p-tolyl)-butene hardly take place. In contrast, when a mixed catalyst comprising lead oxide and/or indium oxide and aluminum oxide, specified by this invention, is used, an isomerization reaction to form dimethylnaphthalenes other than 2,6-dimethylnaphthalene hardly takes place, and the yield of 2,6-dimethylnaphthalene is therefore remarkably improved.

That is, although aluminum oxide and lead oxide and/or indium oxide cannot be individually a catalyst for the production of 2,6-dimethylnaphthalene, a mixture of these can work as an excellent catalyst for the production of 2,6-dimethylnaphthalene. Further, a chromia.alumina catalyst which has been considered to be efficient for the cyclization and dehydrogenation of 2-methyl-1-(p-tolyl)-butene, and a catalyst prepared by incorporating an alkali metal thereinto exhibit degradation in reaction achievement when water is copresent. Differing from these catalysts, the catalyst of this invention exhibits no degradation in reaction achievement even in the copresence of water. Therefore, when the starting material is 2-methyl-1-(p-tolyl)-butene which is prepared by synthesizing p-tolyl-sec-butyl ketone from toluene, butene and carbon monoxide, hydrogenating the carbonyl group of the p-tolyl-sec-butyl ketone to form the corresponding alcohol, and dehydrating the alcohol, the chromia.alumina catalyst or a catalyst prepared by incorporating an alkali metal thereinto require removal of water from the dehydration reaction product before the cyclization and dehydrogenation. However, when the catalyst of this invention is used, the dehydration reaction product is directly usable as a material for the cyclization and dehydrogenation.

In the catalyst of this invention, the amount ratio between lead and/or indium and aluminum (lead and indium/aluminum, lead/aluminum or indium/aluminum) is 0.005 to 0.5 atom/1 atom, preferably 0.01 to 0.3 atom/1 atom.

The method for preparing the catalyst of this invention is not specially limited, and any method may be employed which permits uniform dispersion of lead and/or indium and aluminum on a catalyst surface which contributes to the reaction. For example, the catalyst may be prepared by impregnating alumina with a lead compound and/or an indium compound and drying and calcining the impregnated alumina, by preparing oxide precursors of aluminum and lead as precipitates, respectively, or preparing oxide precursors of aluminum and indium as precipitates, respectively, mixing the precipitates, and drying and calcining the mixture, by preparing oxide precursors of aluminum and lead as a co-precipitate or preparing oxide precursors of aluminum and indium as a coprecipitate and drying and calcining the co-precipitate, or by mixing an oxide precursor of lead or indium or oxide of lead or indium with an alumina sol and drying and calcining the mixture.

When a lead compound is impregnated into alumina, or when the oxide precursor of lead is prepared as a precipitate, used as a lead compound are those lead compounds which can be dissolved in water or a suitable organic solvent such as methanol, and preferred are lead nitrate, lead acetate, lead hydroxyacetate and lead chlorate.

When an indium compound is impregnated into alumina, or when the oxide precursor of indium is prepared as a precipitate, used as an indium compound are those indium compounds which can be dissolved in water or a suitable organic solvent such as methanol, and preferred are indium nitrate, indium sulfate, etc. When an oxide precursor of aluminum is prepared as a precipitate, used as an aluminum compound are those compounds which can be dissolved in water or a suitable organic solvent such as methanol, and preferred are aluminum nitrate, sodium aluminate, aluminum sulfate, aluminum chloride, etc.

The above-prepared catalyst comprising aluminum oxide and lead oxide and/or indium oxide exhibits excellent activity in the cyclization and dehydrogenation of 2-methyl-1-(p-tolyl)-butene, etc. Further improved in activity and selectively is a catalyst which is prepared by incorporating into the above catalyst (comprising aluminum oxide and lead oxide and/or indium oxide) at least one metal oxide selected from alkali metals and alkaline earth metals, at least one metal oxide selected from iron, tin, antimony, chromium, zinc, vanadium, nickel and cobalt, or a combination of at least one metal oxide selected from iron, tin, antimony, chromium, zinc, vanadium, nickel and cobalt with at least one metal oxide selected from alkali metals and alkaline earth metals.

The amount ratio of the above metal oxide selected from alkali metals and alkaline earth metals or the above metal oxide selected from iron, tin, antimony, chromium, zinc, vanadium, nickel and cobalt to lead or indium (above metal/lead or indium) is 0.1 to 10 atoms/1 atom, preferably 0.5 to 5 atoms/1 atom. The method for incorporation of these metals is not specially limited, and any method may be employed which permits homogeneous dispersion of each component on a catalyst surface. For example, the incorporation may be carried out by impregnating the catalyst comprising aluminum oxide and lead oxide and/or indium oxide with a solution of a salt of the above metal, by kneading the catalyst together with a salt of the above metal, by adding a solution of a salt of the above metal when aluminum oxide and lead oxide and/or indium oxide are prepared, by preliminarily preparing oxide precursors of lead and/or indium and the above metal and mixing the oxide precursors with an alumina sol, and by some other methods.

The above-prepared catalyst precursor mixture is dried at a temperature higher than room temperature, preferably at 70° to 130° C., calcined at 300° to 800° C., and optionally molded, whereby the catalyst of this invention is formed.

When 2,6-dimethylnaphthalene is produced by the cyclization and dehydrogenation of 2-methyl-1-(p-tolyl)-butene, etc., in the presence of the catalyst of this invention, the reaction pressure may be any of reduced pressure, atmospheric pressure and elevated pressure. The practically preferred pressure is from atmospheric pressure to 2 kg/cm². The reaction temperature is 350° to 700° C., preferably 450° to 650° C. In addition, when 2-methyl-1-(p-tolyl)-butane is used as a raw material for the cyclization and dehydrogenation, it is desirable to increase the reaction temperature or decrease the space velocity thereof, since the reactivity of 2-methyl-1-(p-tolyl)-butane is a little lower than that of 2-methyl-1-(p-tolyl)-butene when said butene is subjected to cyclization and dehydrogenation. The intended product, 2,6-dimethylnaphthalene, is a solid having a melting point of 106° C., and, operationally and also from the view point of side reaction inhibition, it is desirable to dissolve the material, i.e. 2-methyl-1-(p-tolyl)-butene, etc., in toluene, benzene or steam or dilute the material therewith before the reaction.

For the process of this invention, remarkably generally used materials such as toluene, butene and carbon monoxide can be used as starting materials.

In the process of this invention, 2,6-dimethylnaphthalene is produced through p-tolyl-sec-butyl ketone, which process is nearly free from the formation of isomers other than 2,6-dimethylnaphthalene and gives 2,6-dimethylnaphthalene at high yields.

Therefore, the process of this invention makes it possible to produce highly pure, 2,6-dimethylnaphthalene from such remarkably generally used materials as toluene, butene and carbon monoxide, at a low cost and in a large amount, and therefore, it is industrially important to a great extent.

This invention will be explained in detail below by reference to examples. However, this invention shall not be limited thereto. Catalysts prepared in examples and comparative examples were tested on their activities by charging a silica reaction tube with them, respectively, and carrying out a reaction of a toluene solution of 2-methyl-1-(p-tolyl)-butene or a toluene solution of 2-methyl-1-(p-tolyl)-butane as a raw material.

EXAMPLE 1

32 Grams of lead nitrate was dissolved in 400 ml of ion-exchanged water, 200 g of alumina was added, and the alumina was impregnated with lead by stirring the mixture at 45° C. for 2 hours. The mixture was dried at 70° C. under reduced pressure and calcined in air at 550° C. to give a lead oxide.aluminum oxide catalyst.

EXAMPLE 2

30 Grams of lead nitrate and 310 g of aluminum nitrate (salt nonahydrate) were dissolved in 2 lit. of pure water, and the resultant solution was maintained at 40° C. Separately, 148 g of sodium carbonate was dissolved in 2 lit. of pure water, and the resultant solution was maintained at 40° C. While these two solutions were stirred, the contents were maintained at 40° to 45° C., and these solutions were mixed with each other. And, the resultant mixture was heated to 80° C. to give a precipitate. The precipitate was isolated by filtration, washed with pure water, dried at 110° C., and calcined in air at 550° C. to give a lead oxide.aluminum oxide catalyst.

EXAMPLE 3

160 Grams of lead nitrate was dissolved in 1 lit. of pure water, the resultant solution was maintained at 40° C. Separately, 54 g of sodium carbonate was dissolved in 1 lit. of pure water, and the resultant solution was maintained at 40° C. While these two solutions were stirred, the temperatures of the contents were maintained at 40° to 45° C., and the solutions were mixed with each other. And, the resultant mixture was heated to 80° C. to give a precipitate. The precipitate was isolated by filtration and washed with pure water to give a precipitate of oxide precursor of lead. The precipitate had a lead concentration of 27 wt. %. 150 Grams of this precipitate and 650 g of an alumina sol (alumina content 10 wt. %) were mixed with each other, and the mixture was dried at 110° C. and calcined in air at 550° C. to give a lead oxide.aluminum oxide catalyst.

EXAMPLE 4

50 Grams of the catalyst obtained in Example 1 was added to 124 g of potassium antimonyl tartrate aqueous solution (potassium antimonyl tartrate concentration 5 wt. %), and the mixture was stirred at 45° C. for 2 hours for impregnation. Then, the mixture was dried at 70° C. under reduced pressure, and calcined in air at 550° C. to give a lead oxide.antimony oxide.potassium oxide.aluminum oxide catalyst.

EXAMPLE 5

50 Grams of the catalyst obtained in Example 1 was added to 80 g of stannous sulfate aqueous solution (stannous sulfate concentration 5 wt. %), and the mixture was stirred at 45° C. for 2 hours for impregnation, dried at 70° C. under reduced pressure, and calcined in air at 550° C. to give a lead oxide.tin oxide.aluminum oxide catalyst.

EXAMPLE 6

250 Grams of nickel sulfate (salt hexahydrate) and 160 g of lead nitrate were dissolved to 2 lit. of pure water, and the resultant solution was maintained at 40° C. Separately, 150 g of sodium carbonate was dissolved in 2 lit. of pure water, and the resultant mixture was maintained at 40° C. While these two solutions were stirred, the temperatures of the contents were maintained at 40° to 45° C., and the solutions were mixed with each other. And, the resultant mixture was heated to 80° C. to give a precipitate. The precipitate was isolated by filtration and washed with pure water to obtain a co-precipitate of an oxide precursor of lead and nickel. The co-precipitate had a lead concentration of 16 wt. % and a nickel concentration of 8.3 wt. %. 120 Grams of this co-precipitate was mixed with 1,800 g of an alumina sol (alumina content 10 wt. %), and the resultant mixture was dried at 110° C. and calcined in air at 550° C. to give a lead oxide.nickel oxide.aluminum oxide catalyst.

EXAMPLE 7-10

A calculated amount of a lead oxide.aluminum oxide catalyst prepared in the same way as in Example 1 was added to an aqueous solution of a nitrate of a calculated amount of each metal shown in Table 1, and the resultant mixtures were stirred at 45° C. for 2 hours for impregnation, dried at 70° C. under reduced pressure, and calcined in air at 550° C. to give metal oxide.lead oxide.aluminum oxide catalysts.

EXAMPLE 11

4.63 Grams of calcium nitrate (salt tetrahydrate) and 26 g of lead nitrate were dissolved in 200 ml of ion-exchanged water, and 100 g of alumina was added. The resultant mixture was stirred at 45° C. for 2 hours for impregnation, dried at 70° C. under reduced pressure, and calcined in air at 550° C. to give a calcium oxide.lead oxide.aluminum oxide catalyst.

COMPARATIVE EXAMPLE 1

169 Grams of chromium nitrate (salt nonahydrate) and 28.4 g of potassium nitrate were dissolved in 400 ml of ion-exchanged water, and 200 g of alumina was added. The resultant mixture was stirred at 45° C. for 2 hours for impregnation, dried at 70° C. under reduced pressure and calcined in air at 550° C. to give a potassium oxide.chromium oxide.aluminum oxide catalyst.

COMPARATIVE EXAMPLE 2

The same alumina as that used in Example 1 was used as a catalyst.

COMPARATIVE EXAMPLE 3

The same precipitate of oxide precursor of lead as that obtained in Example 3 was dried at 110° C. and calcined in air at 550° C. to give a lead oxide catalyst.

Table 1 shows the results of Examples 1 to 10 and Comparative Examples 1 to 3.

TABLE 1

| Metal component in catalyst component | Atomic ratio in catalyst | Raw material *1 | Reaction temperature (°C.) | WHSV (1/h) *2 |
|---|---|---|---|---|
| Ex. 1 | Pb—Al | 2:5:100 | 0 | 500 | 1.0 |
|  |  |  | 1 | 520 | 0.5 |
| Ex. 2 | Pb—Al | 11:100 | 0 | 500 | 1.0 |
| Ex. 3 | Pb—Al | 15:100 | 0 | 500 | 1.0 |
| Ex. 4 | K—Sb—Pb—Al | 2:2:2.5:100 | 0 | 500 | 1.0 |
|  |  |  | 1 | 520 | 0.5 |
| Ex. 5 | Sn—Pb—Al | 2:2.5:100 | 0 | 500 | 1.0 |
| Ex. 6 | Ni—Pb—Al | 4.8:2.7:100 | 0 | 500 | 1.0 |
| Ex. 7 | Cr—Pb—Al | 1:2.5:100 | 0 | 500 | 1.0 |
| Ex. 8 | Co—Pb—Al | 3:2.5:100 | 0 | 500 | 1.0 |
| Ex. 9 | Ca—Co—Pb—Al | 0.5:2:2.5:100 | 0 | 500 | 1.0 |
| Ex. 10 | In—Pb—Al | 1.25:2.5:100 | 0 | 500 | 1.0 |
| Ex. 11 | Ca—Pb—Al | 1:4:100 | 0 | 500 | 1.0 |
| CEx. 1 | K—Cr—Al | 7:11:100 | 0 | 500 | 1.0 |
|  |  |  | 1 | 520 | 0.5 |
| CEx. 2 | Al |  | 0 | 500 | 1.0 |
| CEx. 3 | Pb |  | 0 | 500 | 1.0 |

| Metal component in catalyst component | Atomic ratio in catalyst | Conversion (%) | Selectivity to DMN (%) | 2,6-DMN in DMN (%) |
|---|---|---|---|---|
| Ex. 1 | Pb—Al | 2:5:100 | 92 | 75 | 99.2 |
|  |  |  | 88 | 77 | 99.3 |
| Ex. 2 | Pb—Al | 11:100 | 93 | 78 | 99.3 |
| Ex. 3 | Pb—Al | 15:100 | 90 | 77 | 99.2 |
| Ex. 4 | K—Sb—Pb—Al | 2:2:2.5:100 | 92 | 84 | 99.2 |
|  |  |  | 88 | 77 | 99.2 |
| Ex. 5 | Sn—Pb—Al | 2:2.5:100 | 92 | 81 | 99.2 |
| Ex. 6 | Ni—Pb—Al | 4.8:2.7:100 | 93 | 79 | 99.2 |
| Ex. 7 | Cr—Pb—Al | 1:2.5:100 | 92 | 78 | 99.2 |
| Ex. 8 | Co—Pb—Al | 3:2.5:100 | 92 | 77 | 99.2 |
| Ex. 9 | Ca—Co—Pb—Al | 0.5:2:2.5:100 | 87 | 81 | 99.2 |
| Ex. 10 | In—Pb—Al | 1.25:2.5:100 | 90 | 78 | 99.2 |
| Ex. 11 | Ca—Pb—Al | 1:4:100 | 91 | 76 | 99.3 |
| CEx. 1 | K—Cr—Al | 7:11:100 | 90 | 68 | 98.6 |
|  |  |  | 86 | 60 | 99.2 |
| CEx. 2 | Al |  | 93 | 25 | 46.7 |
| CEx. 3 | Pb |  | 43 | trace | — |

Ex. = Example, CEx. = Comparative Example
*1: 0 = toluene solution of 2-methyl-1-(p-tolyl)-butene (2-methyl-1-(p-tolyl)-butene 10 wt. %)
1 = toluene solution of 2-methyl-1-(p-tolyl)-butane (2-methyl-1-(p-tolyl)-butane 10 wt. %)
*2: WHSV = feed amount (g/h)/amount of catalyst (g)
(Reaction pressure = atomospheric pressure)

EXAMPLE 12

32 Grams of indium nitrate (salt trihydrate) was dissolved in 400 ml of ion-exchanged water, and 200 g of alumina was added. The mixture was stirred at 45° C. for 2 hours for impregnation, dried at 70° C. under reduced pressure, and calcined in air at 550° C. to give an indium oxide.aluminum oxide catalyst.

EXAMPLE 13

60 Grams of indium nitrate (salt trihydrate) and 310 g of aluminum nitrate (salt nonahydrate) were dissolved in 2 lit. of pure water, and the resultant solution was maintained at 40° C. Separately, 170 g of sodium carbonate was dissolved in 2 lit. of pure water, and the solution was maintained at 40° C. While these two solutions were stirred, the temperatures of the contents were maintained at 40° to 45° C., and the solutions were mixed with each other. And, the resultant mixture was heated to 80° C. to give a precipitate. The precipitate was isolated by filtration, washed with pure water, dried at 110° C., and calcined in air at 550° C. to give an indium oxide.aluminum oxide catalyst.

EXAMPLE 14

50 Grams of indium sulfate (salt nonahydrate) was dissolved in 0.4 lit. of pure water, and the resultant solution was maintained at 40° C. Separately, 25 g of sodium carbonate was dissolved in 0.4 lit. of pure water, and the resultant solution was maintained at 40° C. While these two solutions were stirred, the temperatures of the contents were maintained at 40° to 45° C., and these two solutions were mixed with each other. And, the resultant mixture was heated to 80° C. to give a precipitate. The precipitate was isolated by filtration and washed with pure water to give a precipitate of an oxide precursor of indium. The precipitate had an indium concentration of 27 wt. %. 60 Grams of this precipitate was mixed with 650 g of an alumina sol (alumina content 10 wt. %), and the mixture was dried at 110° C. and calcined in air at 550° C. to give an indium oxide.aluminum oxide catalyst.

EXAMPLE 15

50 Grams of the catalyst obtained in Example 12 was added to 124 g of a potassium antimonyl tartrate aqueous solution (potassium antimonyl tartrate concentration 5 wt. %), and the mixture was stirred at 45° C. for 2 hours for impregnation, dried at 70° C. under reduced pressure and calcined in air at 550° C. to give an indium oxide.antimony oxide.potassium oxide.aluminum oxide catalyst.

EXAMPLE 16

50 Grams of the catalyst obtained in Example 12 was added to 160 g of a stannous sulfate aqueous solution (stannous sulfate concentration 5 wt. %), and the resultant mixture was stirred at 45° C. for 2 hours for impregnation, dried at 70° C. under reduced pressure and calcined in air at 550° C. to give an indium oxide.tin oxide.aluminum oxide catalyst.

EXAMPLE 17

65 Grams of nickel nitrate (salt hexahydrate) and 160 g of indium nitrate were dissolved in 2 lit. of pure water, and the resultant mixture was maintained at 40° C. Separately, 100 g of sodium carbonate was dissolved in 2 lit. of pure water and the resultant mixture was maintained at 40° C. While these two solutions were stirred, the temperatures of the contents were maintained at 40° to 45° C., and these two solutions were mixed with each other. And, the resultant mixture was heated to 80° C. to give a precipitate.

The precipitate was isolated by filtration, and washed with pure water to give a co-precipitate of oxide precursor of indium and nickel. The co-precipitate had an indium concentration of 16 wt. % and a nickel concetration of 4.1 wt. %. 120 Grams of the co-precipitate was mixed with 1,800 g of an alumina sol (alumina content 10 wt. %), and the resultant mixture was dried at 110° C. and calcined in air at 550° C. to give an indium oxide.nickel oxide.aluminum oxide catalyst.

EXAMPLES 18–21

A calcilated amount of a indium oxide.aluminum oxide catalyst prepared in the same way as in Example 12 was added to an aqueous solution of a nitrate of a calculated amount of each metal shown in Table 2, and the resultant mixtures were stirred at 45° C. for 2 hours for impregnation, dried at 70 under reduced pressure, and calcined in air at 550° C. to give metal oxide.indium oxide.aluminum oxide catalysts.

EXAMPLES 22–24

A calculated amount of an indium oxide.aluminum oxide catalyst prepared in the same way as in Example 14 was added to an aqueous solution of a nitrate of a calculated amount of each metal shown in Table 2, and the resultant mixtures were stirred at 45° C. for 2 hours for impregnation, dired at 70° C. under reduced pressure and calcined in air at 550° C. to give metal oxide.indium oxide.aluminum oxide catalysts.

COMPARATIVE EXAMPLE 4

The same precipitate of oxide precursor of indium as that obtained in Example 14 was dried at 110° C. and calcined in air at 550° C. to give an indium oxide.

Table 2 shows the results of Examples 12 to 24 and Comparative Example 4.

TABLE 2

| Metal component in catalyst component | Atomic ratio in catalyst | Raw Material *1 | Reaction temperature (°C.) | WHSV (1/h) *2 |
| --- | --- | --- | --- | --- |
| Ex. 12 In—Al | 2.3:100 | 0 | 500 | 1.0 |
| | | 1 | 520 | 0.5 |
| Ex. 13 In—Al | 20:100 | 0 | 500 | 1.0 |
| Ex. 14 In—Al | 11:100 | 0 | 500 | 1.0 |
| Ex. 15 K—Sb—In—Al | 2:2:2.3:100 | 0 | 500 | 1.0 |
| | | 1 | 520 | 0.5 |
| Ex. 16 Sn—In—Al | 4:2.3:100 | 0 | 500 | 1.0 |
| Ex. 17 Ni—In—Al | 2.4:4.7:100 | 0 | 500 | 1.0 |
| Ex. 18 Cr—In—Al | 1:2.3:100 | 0 | 500 | 1.0 |
| Ex. 19 Co—In—Al | 3:2.3:100 | 0 | 500 | 1.0 |
| Ex. 20 Ca—In—Al | 0.7:2.3:100 | 0 | 500 | 1.0 |
| Ex. 21 Ca—Co—In—Al | 0.3:2:2.3:100 | 0 | 500 | 1.0 |
| Ex. 22 Fe—In—Al | 20:11:100 | 0 | 500 | 1.0 |
| Ex. 23 Zn—In—Al | 5:11:100 | 0 | 500 | 1.0 |
| Ex. 24 V—In—Al | 5:11:100 | 0 | 500 | 1.0 |
| CEx. 4 In | | 0 | 500 | 1.0 |

| Metal component in catalyst component | Atomic ratio in catalyst | Conversion (%) | Selectivity to DMN (%) | 2,6-DMN in DMN (%) |
| --- | --- | --- | --- | --- |
| Ex. 12 In—Al | 2.3:100 | 90 | 77 | 99.2 |
| | | 86 | 79 | 99.3 |
| Ex. 13 In—Al | 20:100 | 90 | 78 | 99.3 |
| Ex. 14 In—Al | 11:100 | 88 | 77 | 99.2 |
| Ex. 15 K—Sb—In—Al | 2:2:2.3:100 | 92 | 83 | 99.2 |
| | | 88 | 76 | 99.2 |
| Ex. 16 Sn—In—Al | 4:2.3:100 | 90 | 84 | 99.2 |
| Ex. 17 Ni—In—Al | 2.4:4.7:100 | 90 | 78 | 99.2 |
| Ex. 18 Cr—In—Al | 1:2.3:100 | 90 | 78 | 99.2 |
| Ex. 19 Co—In—Al | 3:2.3:100 | 92 | 76 | 99.2 |
| Ex. 20 Ca—In—Al | 0.7:2.3:100 | 88 | 77 | 99.3 |
| Ex. 21 Ca—Co—In—Al | 0.3:2:2.3:100 | 87 | 82 | 99.2 |
| Ex. 22 Fe—In—Al | 20:11:100 | 88 | 78 | 99.2 |
| Ex. 23 Zn—In—Al | 5:11:100 | 90 | 77 | 99.3 |
| Ex. 24 V—In—Al | 5:11:100 | 92 | 79 | 99.2 |

TABLE 2-continued

| CEx. 4 | In | 53 | 38 | 51.8 |

Ex. = Example, CEx. = Comparative Example
*1: 0 = toluene solution of 2-methyl-1-(p-tolyl)-butene (2-methyl-1-(p-tolyl)-butene 10 wt. %)
1 = toluene solution of 2-methyl-1-(p-tolyl)-butane (2-methyl-1-(p-tolyl)-butane 10 wt. %)
*2: WHSV = feed amount (g/h)/amount of catalyst (g)
(Reaction pressure = atomospheric pressure)

What is claimed is:

1. A process for producing 2,6-dimethylnaphthalene, which comprises subjecting 2-methyl-1-(p-tolyl)-butene, 2-methyl-1-(p-tolyl)-butane or a mixture of these to cyclization and dehydrogenation in the presence of a catalyst comprising lead oxide and/or indium oxide and aluminum oxide.

2. A process according to claim 1, wherein the catalyst further contains oxide of at least one metal selected from the group consisting of alkali metals and alkaline earth metals.

3. A process according to claim 1, wherein the catalyst further contains oxide of at least one metal selected from the group consisting of iron, tin, antimony, chromium, zinc, vanadium, nickel and cobalt.

4. A process according to claim 1, wherein the catalyst further contains oxide of at least one metal selected from the group consisting of alkali metals and alkaline earth metals and oxide of at least one metal selected from the group consisting of iron, tin, antimony, chromium, zinc, vanadium, nickel and cobalt.

5. A process according to claim 1, wherein the catalyst contains 0.005 to 0.5 atom of lead and/or indium per atom of aluminum.

6. A process according to claim 1, wherein the catalyst contains 0.01 to 0.3 atom of lead and/or indium per atom of aluminum.

7. A process according to claim 2, wherein the catalyst contains 0.1 to 10 atoms of at least one metal recited in claim 2 per atom of lead and/or per atom of indium.

8. A process according to claim 3, wherein the catalyst contains 0.1 to 10 atoms of at least one metal recited in claim 3 per atom of lead and/or per atom of indium.

9. A process according to claim 4 wherein the catalyst contains 0.1 to 10 atoms of at least one metal selected from the group consisting of alkali metals and alkaline earth metals and least one metal selected from the group consisting of iron, tin, antimony, chromium, zinc, vanadium, nickel and cobalt.

* * * * *

UNITED STATES PATENT AND TRADEMARK OFFICE
CERTIFICATE OF CORRECTION

PATENT NO. : 5,068,480

DATED : November 26, 1991

INVENTOR(S) : Makoto TAKAGAWA, Ken YAMAGISHI, Jyun YOSHIHARA, Kenji INAMASA, Kumiko WATABE It is certified that error appears in the above-identified patent and that said Letters Patent is hereby corrected as shown below:

Column 12:

Claim 9, line 3 from the bottom, after "and" insert -- at --.

Signed and Sealed this

Sixth Day of July, 1993

Attest:

MICHAEL K. KIRK

Attesting Officer

Acting Commissioner of Patents and Trademarks